United States Patent
Perrot et al.

(10) Patent No.: US 11,826,100 B2
(45) Date of Patent: Nov. 28, 2023

(54) WEARABLE BINOCULAR OPTOELECTRONIC DEVICE FOR MEASURING LIGHT SENSITIVITY THRESHOLD OF A USER

(71) Applicant: Essilor International, Charenton-le-Pont (FR)

(72) Inventors: Stéphane Perrot, Charenton-le-Pont (FR); Amandine Debieuvre, Charenton-le-Pont (FR); Sylvain Chene, Charenton-le-Pont (FR); Florian Caleff, Charenton-le-Pont (FR); Loïc Baillon, Charenton-le-Pont (FR); Anne-Catherine Scherlen, Charenton-le-Pont (FR); Sarah Marie, Charenton-le-Pont (FR); Susana Montecelo, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 634 days.

(21) Appl. No.: 16/969,626

(22) PCT Filed: Feb. 13, 2019

(86) PCT No.: PCT/EP2019/053545
§ 371 (c)(1),
(2) Date: Aug. 13, 2020

(87) PCT Pub. No.: WO2019/158582
PCT Pub. Date: Aug. 22, 2019

(65) Prior Publication Data
US 2020/0397280 A1    Dec. 24, 2020

(30) Foreign Application Priority Data
Feb. 13, 2018   (EP) .................................... 18305146

(51) Int. Cl.
*A61B 3/06*   (2006.01)
*A61B 3/00*   (2006.01)
(Continued)

(52) U.S. Cl.
CPC ............ *A61B 3/063* (2013.01); *A61B 3/0008* (2013.01); *G01N 21/01* (2013.01); *G01N 21/4738* (2013.01); *G01N 2021/0112* (2013.01)

(58) Field of Classification Search
CPC ...... A61B 3/063; A61B 3/0008; G01N 21/01; G01N 2021/0112; G01N 21/4738
(Continued)

(56) References Cited

U.S. PATENT DOCUMENTS

| | | | |
|---|---|---|---|
| 2,916,963 | A | 12/1959 | Bouman |
| 4,784,483 | A | 11/1988 | Holladay et al. |

(Continued)

FOREIGN PATENT DOCUMENTS

| | | |
|---|---|---|
| EP | 1 345 656 B1 | 7/2008 |
| EP | 2 853 937 | 4/2015 |

(Continued)

OTHER PUBLICATIONS

International Search Report for PCT/EP2019/053545 dated Apr. 25, 2019, 4 pages.
(Continued)

*Primary Examiner* — William R Alexander
*Assistant Examiner* — Sharrief I Broome
(74) *Attorney, Agent, or Firm* — NIXON & VANDERHYE

(57) ABSTRACT

Disclosed is a binocular optoelectronic device wearable by a user for measuring a light sensitivity threshold of the user, including: a diffuser configured to face eyes of the user; at least one light source for emitting light toward the diffuser. The diffuser includes predetermined parameters allowing to
(Continued)

provide a quasi-homogeneous light diffusion to at least one eye of the user from light emitted by the at least one light source.

20 Claims, 4 Drawing Sheets

(51) Int. Cl.
  *G01N 21/01* (2006.01)
  *G01N 21/47* (2006.01)
(58) Field of Classification Search
  USPC ................................ 351/220, 219, 216, 222
  See application file for complete search history.

(56) References Cited

U.S. PATENT DOCUMENTS

| | | | | |
|---|---|---|---|---|
| 5,114,222 | A * | 5/1992 | Cornsweet | A61B 3/024 351/204 |
| 6,062,710 | A * | 5/2000 | Hewitt | F21V 5/002 362/311.03 |
| 6,099,126 | A | 8/2000 | Teskey | |
| 2003/0174283 | A1 | 9/2003 | Epitropoulos | |
| 2012/0008091 | A1 * | 1/2012 | Stewart | A61B 3/063 351/246 |
| 2015/0245767 | A1 * | 9/2015 | Northcott | G06V 10/143 351/206 |
| 2016/0380161 | A1 * | 12/2016 | Rindt | C03B 19/101 257/81 |
| 2017/0325676 | A1 | 11/2017 | Lichtenauer et al. | |

FOREIGN PATENT DOCUMENTS

| | | | | |
|---|---|---|---|---|
| EP | 2853937 A1 * | 4/2015 | ............. | A61B 3/112 |
| JP | 2001-070244 A | 3/2001 | | |
| JP | 2004-524067 A | 8/2004 | | |
| JP | 2014-198096 A | 10/2014 | | |
| JP | 2017-512543 A | 5/2017 | | |
| WO | WO-2012006330 A1 * | 1/2012 | ............. | A61B 3/063 |
| WO | 2015/138963 A1 | 9/2015 | | |

OTHER PUBLICATIONS

Written Opinion of the ISA for PCT/EP2019/053545 dated Apr. 25, 2019, 5 pages.
European Search Report for EP 18 30 5146 dated Aug. 23, 2018, 6 pages.
Office Action issued in Japanese Patent Application No. 2020-543380 dated Dec. 5, 2022.

* cited by examiner

WEARABLE BINOCULAR OPTOELECTRONIC DEVICE FOR MEASURING LIGHT SENSITIVITY THRESHOLD OF A USER This application is the U.S. national phase of International Application No. PCT/EP2019/053545 filed Feb. 13, 2019 which designated the U.S. and claims priority to EP Patent Application No. 18305146.5 filed Feb. 13, 2018, the entire contents of each of which are hereby incorporated by reference.

BACKGROUND OF THE INVENTION

Field of the Invention

The invention relates to the field of the measurement of light sensitivity. Particularly, the invention is directed to a wearable binocular optoelectronic device for measuring light sensitivity threshold of a user. The invention further concerns a method for measuring a light sensitivity threshold of a user using such a binocular optoelectronic device.

Description of the Related Art

Comfort and visual acuity of a subject may vary depending on the lenses filtering properties applied to lenses worn by said subject. Lenses filtering properties notably comprise intensity, spectral or intensity spatial repartition filtering properties. It is known from the art to determine the light sensitivity of a subject before prescribing tinted lenses to provide him with the most appropriate tinted lenses. Particularly, it is known from the art to measure the subject's light sensitivity by exposing the subject to glare or light possessing significant intensity.

For example, it is known from U.S. Pat. No. 6,099,126 an interactive testing system comprising an imaging device for displaying images upon a viewing screen set at a predetermined distance from an observation area from which an observer may view the images. An illumination source projects varying degrees of intensity onto the screen resulting in possible discomfort to the observer's eyes. A response indicator controlled by the observer indicates at which point the light intensity causes such discomfort and determines the need for filtering lenses.

Said interactive testing system has significant bulkiness and heaviness that requires to dispose this system on a support, as a table. Therefore, this interactive testing system is difficult to move so that it is intended to be stationary. This may render the measurement of the subject's light sensitivity laborious and not practical.

Furthermore, said interactive testing system allows to determine at which point particular light conditions in the device cause discomfort to the subject. However, it is not possible to determine a light sensitivity threshold of the subject corresponding to an effective luminance. Indeed, light in the interactive testing system is not homogeneous enough to determine such a threshold.

Another example of light sensitivity measurement system is U.S. Pat. No. 4,784,483 A which describes a monocular brightness acuity tester allowing to assess functional visual acuity in bright light conditions and to test for recovery of visual activity after photostressing the retina of a subject. Said tester comprises a device forming a cavity intended to be disposed in front of a subject's eye. The cavity comprises an aperture allowing the subject to see through the tester. Furthermore, a source of illumination is provided in the cavity to simulate bright light condition in the cavity.

However, said monocular brightness acuity tester does not allow to determine a light sensitivity threshold of the subject corresponding to an effective luminance. Indeed, it has been observed that light sensitivity threshold is a global value that can be only determined globally, i.e. by simultaneously testing both eyes of the subject. Furthermore, said brightness acuity tester is not configured to provide a sufficient homogeneity to the subject's eye.

A problem that the invention aims to solve is thus to provide a portable binocular device configured to provide sufficient light homogeneity for measuring light sensitivity threshold of a user.

SUMMARY OF THE INVENTION

To solve this problem, the invention provides a binocular optoelectronic device wearable by a user for measuring a light sensitivity threshold of the user, comprising:
  a diffuser configured to face eyes of the user,
  at least one light source for emitting light toward said diffuser,
wherein the diffuser comprises predetermined parameters allowing to provide a quasi-homogeneous light diffusion to at least one eye of the user from light emitted by said at least one light source.

Providing a binocular optoelectronic device with a light source and a diffuser configured to provide quasi-homogeneous light diffusion allows to simultaneously glare both user's eyes with a quasi-homogeneous light. In doing so, it is possible to precisely measure a light sensitivity threshold of the user.

Furthermore, the wearable configuration of the binocular optoelectronic device enables easy handling of the device so that a light sensitivity threshold measurement may be performed quickly. Combining a precise measurement with easy and practical handling allows to consider new uses for the device. Indeed, said binocular optoelectronic device may be used directly by the eye care professional without the need of a bulky measurement machine. Said device may also be used by the user himself at home or in various conditions, for example by measuring its light sensitivity threshold at different times of the day, months and/or years.

Moreover, such predetermined parameters of the diffuser allow to obtain a quasi-homogeneity diffusion with lower energy consumption of the light source with respect to known devices. It is particularly useful for a wearable device that consequently needs batteries with reduced power energy.

According to an embodiment of the binocular optoelectronic device, said predetermined parameters comprise at least one among: shape, geometry and material of the diffuser.

According to an embodiment of the binocular optoelectronic device, said predetermined parameters allow to provide a light diffusion with a homogeneity of at least 55%, preferably at least 60%, preferably at least 70%, 80%, preferably of at least 90%, most preferably of at least 95%.

According to an embodiment of the binocular optoelectronic device, the homogeneity being determined based on the luminance distribution diffused by the diffuser and projected on a planar measuring surface, the homogeneity is determined with regard to at least one predetermined area of said planar measuring surface.

According to an embodiment of the binocular optoelectronic device, said at least predetermined area is circular.

According to an embodiment of the binocular optoelectronic device, said predetermined parameters allows to provide a light diffusion with a homogeneity of:
- at least 55% with a predetermined area equal or lower than 4245 mm², and/or
- at least 74% with a predetermined area equal or lower than 1060 mm², and/or
- at least 76% with a predetermined area equal or lower than 470 mm², and/or
- at least 84% with a predetermined area equal or lower than 115 mm², and/or
- at least 85% with a predetermined area equal or lower than 29 mm².

According to an embodiment of the binocular optoelectronic device, said diffuser is concave.

According to an embodiment of the binocular optoelectronic device, said diffuser comprises at least two concave portions having a centre of curvature distinct from each other.

According to an embodiment of the binocular optoelectronic device, at least one among said at least two concave portions is at least partially spherical, the centre of curvature of said at one among said at least two concave portions being the centre of the sphere.

According to an embodiment of the binocular optoelectronic device, the diffuser is configured to dispose the centre of curvature of a concave portion between an eye of the user and said concave portion.

According to an embodiment of the binocular optoelectronic device, the binocular optoelectronic device is dimensioned to receive therein an optical device worn by the user.

According to an embodiment of the binocular optoelectronic device, said at least one light source is disposed at the periphery of the diffuser.

According to an embodiment of the binocular optoelectronic device, said at least one light source comprises a light emitting axis oriented toward at least one among said centres of curvature.

According to an embodiment of the binocular optoelectronic device, the diffuser comprises an internal surface having an albedo of at least 80%, preferably of at least 90%, most preferably of at least 95%.

According to an embodiment of the binocular optoelectronic device, it further comprises at least one among:
- a sensor configured to determine at least one user parameter representative of the light sensitivity of the user,
- a controller configured to provide at least one among: controlling the luminance of light emitted by said at least one light source, controlling the duration of the light emission, spatial repartition of the light emission and the spectrum of the light emission.

The invention further provides a method for measuring a light sensitivity threshold of a user, comprising:
- providing a user with a binocular optoelectronic device as described above,
- providing the user with a quasi-homogeneous light diffusion from light emitted by said at least one light source,
- determining a light sensitivity threshold of the user depending of user parameter.

According to an embodiment of the measuring method, the step of providing the user with a quasi-homogeneous light diffusion comprises a step of varying the luminance of light emitted by said at least one light source.

According to an embodiment of the measuring method, it further comprises during the varying step:
- detecting a first user parameter representative of a first light sensitivity value of the user at a first luminance value,
- detecting a second user parameter representative of a second light sensitivity value of the user at a second luminance value, wherein said light sensitivity threshold is determined depending on at least one among the first and second user parameters.

BRIEF DESCRIPTION OF THE DRAWINGS

The invention is described in more detail below by way of the figures that show only one preferred embodiment of the invention.

DESCRIPTION OF THE PREFERRED EMBODIMENTS

Figure 1:
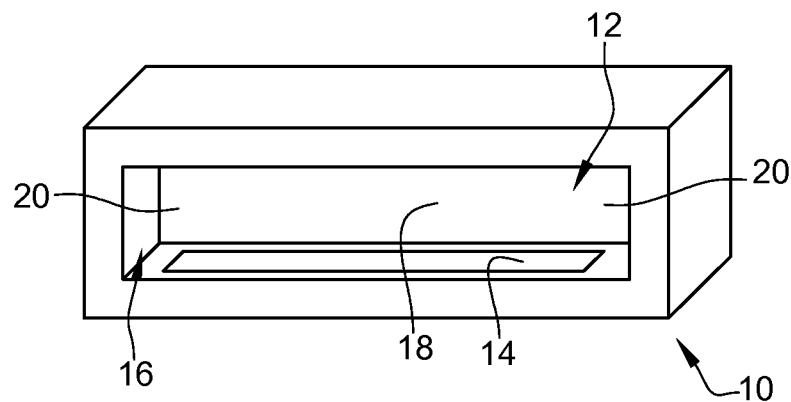
FIG. 1 schematically shows a perspective view of an embodiment of a binocular optoelectronic device comprising a planar diffuser.

The present invention provides a binocular optoelectronic device and a method for measuring a light sensitivity threshold of a user.

By "sensitivity to light" of the user, what is meant is any relatively intense and prolonged reaction or modification of comfort or visual performance in relation to a temporary or continuous light flux or stimuli.

The quantity representative of the sensitivity of the eye of the user to said characteristic light flux is the light sensitivity threshold and is chosen from at least one of the following quantities:
- an objective physiological measurand of the user,
- an objective physical measurand of the user,
- a subjective measurand related to the perception or to the expression of the user.

By "objective physiological measurand" of the user, what is meant is any value relative to the measurement of at least one parameter or of at least one characteristic related to the integrity and to the operation of a component of the ocular system or of structures related to this system. The choice of such a representative quantity allows the physiological capacities of the eye or of related elements to treat all or some of the characteristics of the characteristic light flux to be evaluated. This analysis allows the conditions under or situations in which the user will not be able to naturally manage the light flux to be identified. The prescription of a filter will then allow the associated loss of vision and/or visual comfort to be compensated for.

By "objective physical measurand" of the user, what is meant is any value relative to the measurement of at least one parameter characteristic of a state of the structure and ocular functions or of the related structures via an optical and/or photometric measurement. The addition of a physical gauge allows a component of the ocular or related structure to be characterized and quantified inferentially. The choice of such a representative quantity makes it possible to quantify, via a physical measurement, the capacities and performance of one or more ocular or related structures in relation with the glare processes. Depending on the studied structure and the results obtained, the characteristics of the filter will be orientated differently in order to optimize the comfort and/or visual performance depending on the fragility/fragilities of the ocular and related structure in question.

By "subjective measurand related to the perception or to the expression" of the user, what is meant is all the verbal responses expressed by the user or any action of the user representative of its discomfort or visual perception. The choice of such a representative quantity allows the visual performance and/or visual discomfort experienced and expressed by the user to be determined subjectively. This evaluation allows the conditions under or situations in which the user obtains an optimal comfort and optimal performance, and also the conditions of discomfort and/or loss of visual performance, to be defined.

As shown on FIG. 1, a binocular optoelectronic device 10 comprises a diffuser 12 configured to face eyes of a user when the binocular optoelectronic device 10 is used. The binocular optoelectronic device 10 further comprises at least one light source 14 for emitting light toward said diffuser 12. Said light source 14 and diffuser 12 are preferably lodged in a cavity 16 formed by the binocular optoelectronic device 10. The diffuser 12 forms at least partially a bottom surface of the cavity 16 so as to face user's eyes when positioned in front of the cavity 16. Providing the binocular optoelectronic device 10 with a cavity 16 into which the diffuser 12 is formed allows to improve the homogeneity of light diffusion. Alternatively, the binocular optoelectronic device 10 may be formed without any cavity 16 if the diffuser 12 and the light source 14 provides a sufficient light homogeneity to the user's eyes.

Light source 14 extends at least partially along the diffuser 12. In a general way, light source 14 may be disposed in any position allowing to emit light toward the diffuser 12. Preferably, light source 14 is disposed at the periphery of the diffuser 12 to facilitate light emission toward the diffuser 12. A plurality of light sources 14 may be provided to emit light toward the diffuser 12. In this case, light sources 14 may be positioned to selectively emit light toward certain areas of the diffuser 12. As shown on FIG. 1, light source 14 may be disposed along a bottom area 18 of the diffuser 12. Alternatively or in combination, light source 14 may be disposed along one or more side areas 20 and/or along an upper area (not shown) of the diffuser 12 to emit light toward the diffuser 12. Binocular optoelectronic device 10 may also be configured to act as a monocular optoelectronic device by emitting light toward only one side of the diffuser 12.

Light source 14 preferably comprises at least one light-emitting diode (LED) able to have variable light spectrum as RGB LEDs (Red-Green-Blue light emitting diodes) or RGB-W LEDs ((Red-Green-Blue-White light emitting diodes). Alternatively, light source 14 may be configured to provide a predetermined single white light spectrum or, alternatively, a spectrum having all visible radiations with substantially the same intensity, in contrast with a spectrum having peaks. Said at least one light source 14 is preferably controlled with a constant current to obtain a constant light flux coming out said at least one light source 14. Providing the user with a constant light flux allows to reduce or avoid biological effects disturbances compared to light sources controlled with Pulse Width Modulation (PWM).

Furthermore, when the binocular optoelectronic device 10 comprises a plurality of light sources 14, at least one light source 14 may be disposed at a median area of the diffuser 12 to face at least one eye of the user. In this case, said at least one light source 14 forms a punctual light source configured to emit light toward at least one eye of the user. When such a punctual light source is combined with homogeneous light diffusion, the binocular optoelectronic device 10 is configured to expose the user to either a homogeneous light or punctual light, or both simultaneously.

Diffuser 12 is configured to provide the user's eyes with a diffused light when enlightened by the light source 14. Particularly, diffuser 12 comprises predetermined parameters allowing to provide a quasi-homogeneous light diffusion to at least one eye of the user from light emitted by said at least one light source 14. Preferably, said quasi-homogeneous light diffusion is provided to both eyes of the user. By "quasi-homogeneous light diffusion", we mean light diffusion with a homogeneity of at least 55%, preferably at least 60%, preferably at least 70%, preferably at least 80%, preferably of at least 90%, most preferably of at least 95%. Homogeneity is determined depending on the luminance distribution of the light flux provided by the diffuser 12. Particularly, homogeneity is determined depending on a maximum and a minimum values of the luminance distribution of the light flux provided in any point of the diffuser 12. Homogeneity may be obtained using the following equation:

$$H(\%) = [1 - ((L\max - L\min)/L\max)] * 100$$

wherein:
H (%) is the percentage of homogeneity
Lmax is the maximum luminance value (cd/m$^2$)
Lmin is the minimum luminance value (cd/m$^2$).

Maximum and minimum values of the luminance distribution may be obtained with a cartography of the luminance distribution of the diffuser (see FIG. 6 described below). Alternatively, said maximum and minimum values of the luminance distribution may be obtained by calculating the illumination level at predetermined points of the diffuser 12. According to a preferred embodiment, the homogeneity of the diffuser surface is determined by considering the luminance distribution of the diffuser surface projected on a planar measuring surface. This planar measuring surface corresponds to a 2D representation of the light flux received by a user. An example of such a planar measuring surface is shown on FIG. 6. The planar measuring surface is preferably oriented so as to face the surface diffuser 12. Most preferably, the planar measuring surface is oriented to be included or parallel to an orientation plane defined by the binocular optoelectronic device 10. This orientation plane may be defined as being a plane including at least three positioning points belonging to at least one positioning surface of the binocular optoelectronic device 10. This at least one positioning surface comprises for example surfaces intended to contact the forehead and the nose of the user.

Figure 5:
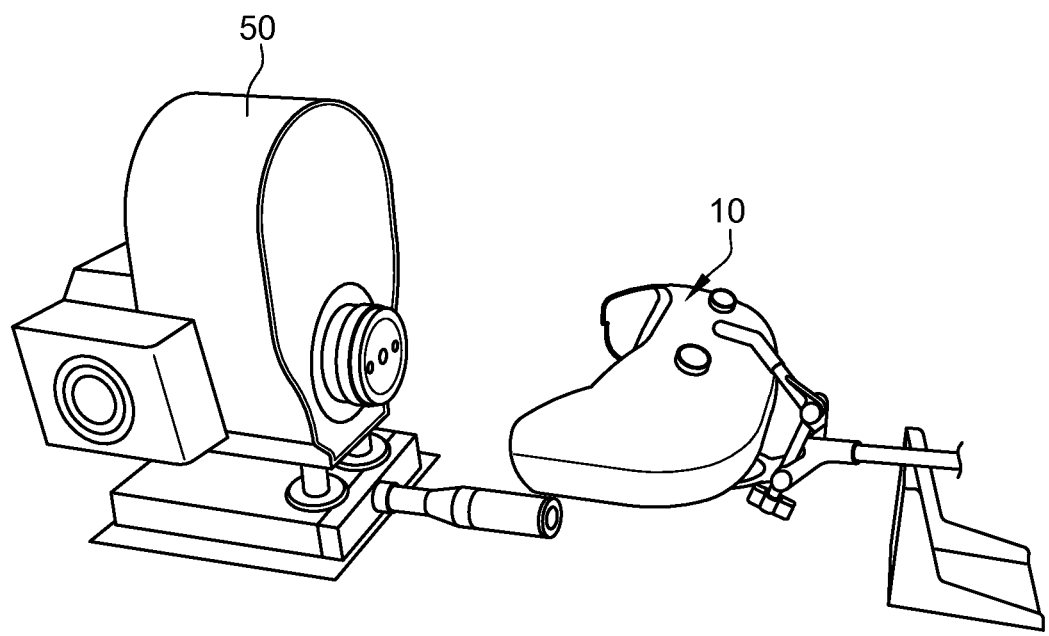
FIG. 5 schematically shows a test bench for obtaining a cartography of the luminance distribution of the light diffused by the diffuser.

This illumination level may be obtained with a spectrometer combined to a cosine receiving fiber or an imaging spectro-colorimeter. Particularly, as shown on FIG. 5, a measurement process may be performed by disposing a measuring device 50 in front of the diffuser 12. Particularly, the measuring device 50 used in the test bench shown on FIG. 5 is an imaging spectro-colorimeter called MURATest®. The lens of the measuring device 50 is preferably positioned at a distance of 45 cm from the diffuser 12. Said at least one light source 14 is powered on to emit light toward the diffuser 12. Then, the light diffusion provided by the diffuser 12 is measured by the measuring device 50 to obtain the luminance distribution projected on the planar measuring surface. The measuring device 50 allows to measure the illumination level of a plurality of points of the planar measuring surface. The homogeneity is then obtained using the equation provided above. The measuring device 50 is positioned so that its lens axis is perpendicular to said orientation plane.

Preferably, the homogeneity is determined for different light intensities of the light source 14 to average the homogeneity. Furthermore, the homogeneity may be determined for different colors of light to obtain homogeneity values reflecting cold or warm light. Emitting light reflecting a cold or warm light, e.g. by emitting blue or red light, allows to respectively simulate substantially artificial or natural light.

Furthermore, homogeneity of light diffusion may be determined for the whole surface of the diffuser 12 or, alternatively, for only predetermined areas of the diffuser surface. Thus, homogeneity may be determined only for areas of the diffuser located in front of user's eyes, e.g. a left and a right areas of the diffuser surface each configured to face an eye of the user. Hence, quasi-homogeneity may be determined for an area of the diffuser surface, preferably at least one surface area facing at least one user's eye. Similarly, in the preferred embodiment wherein the homogeneity is measured on a projected planar measuring surface 52, homogeneity may be determined for the whole surface of the planar measuring surface or, alternatively, for only predetermined areas of the planar measuring surface. Homogeneity may thus be determined for one or more areas of the planar measuring surface facing user's eyes, e.g. a left and a right areas of the planar measuring surface each configured to face an eye of the user. In a preferred embodiment, the left and right areas are positioned so as to be centered with regard to each user's eye. In other words, if the predetermined area is circular, the center of the circle is positioned on the line of sight of the corresponding eye when the user looks straight ahead.

Predetermined area preferably comprises at least one circular area 54 facing a user's eye. This circular shape allows to approximately define an area corresponding to the light diffusion received by the user's eye. The circular area has for example a diameter of lower than or equal to 52 mm, preferably lower than or equal to 26 mm, preferably lower than or equal to 17.3 mm, preferably lower than or equal to 8.7 mm, preferably lower than or equal to 4.3 mm. Said examples of circular areas 54 are shown on FIG. 7. Tests performed to determine the light homogeneity diffused by the diffuser 12 using these circular areas 54 are described below.

Said predetermined parameters comprise at least one among: shape, geometry and material of the diffuser 12.

Regarding shape parameter, diffuser 12 may be of any shape allowing to provide quasi-homogeneous light diffusion when enlightened by the light source 14. As shown on FIG. 1, diffuser 12 may be planar. In this case, the light source 14 is selectively disposed to emit light toward the diffuser 12 with a various intensity along the diffuser 12. Indeed, when the diffuser 12 is planar a light diffusion with less homogeneity is observed toward the periphery of the diffuser 12. Therefore, a plurality of light sources 14 is preferred when the diffuser 12 is planar to facilitate the variable enlightenment of the diffuser 12.

Figure 2:
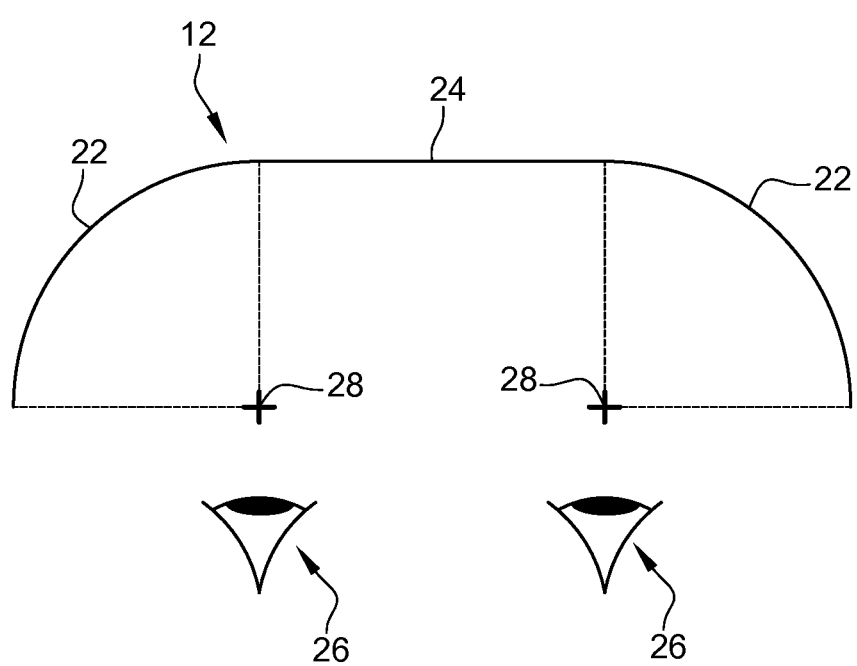
FIG. 2 schematically shows a cross section profile of an embodiment of a concave diffuser.

Alternatively, diffuser 12 may be concave. The centre of curvature of said concavity may be configured to improve homogeneity of light diffusion. For example, said diffuser 12 may comprise at least two concave portions having a centre of curvature distinct from each other. FIG. 2 shows an example of a profile of a diffuser 12 comprising two concave portions 22 disposed on each side of a planar central portion 24. Each concave portion 22 is configured to be disposed in front of an eye 26 of the user when the binocular optoelectronic device 10 is worn. These concave portions 22 enable to direct light rays emitted by the light source 14 toward user's eyes so as to improve homogeneity of light diffusion. In the case where concave portions 22 are partially cylindrical, a variable enlightenment of the diffuser 12 is preferable along cylinder's generatrix to ensure that light diffusion is at least quasi-homogeneous. Particularly, a larger number of light sources 14 or light sources with more intensity is preferable toward the periphery of the cylinder's generatrix. When the diffuser 12 is concave, at least one light source 14 comprises a light emitting axis oriented toward the centre of curvature of the concavity. In the case where the diffuser 12 comprises two concave portions, said at least one light source 14 comprises a light emitting axis oriented toward at least one among said centres of curvature.

Figure 3:
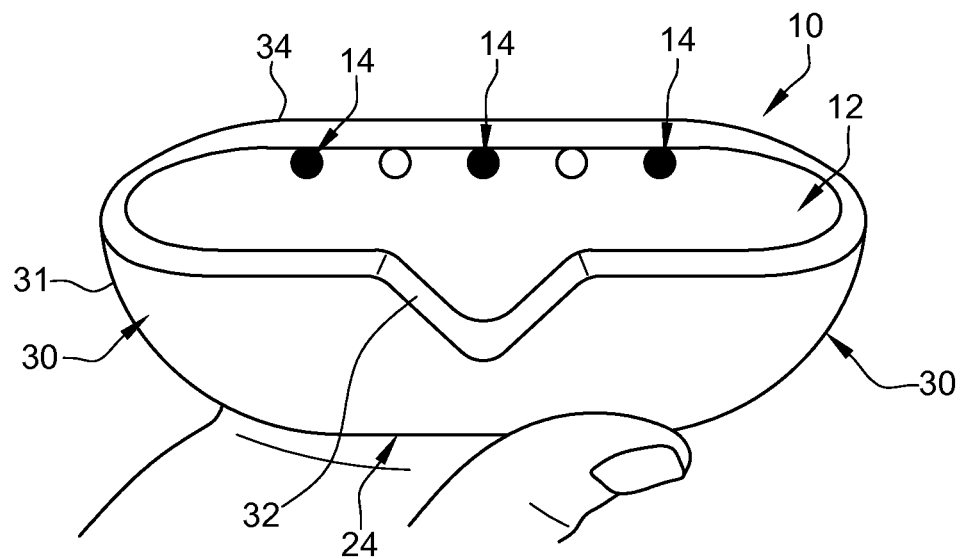
FIGS. 3 and 4 schematically show perspective views of an embodiment of a binocular optoelectronic device comprising a partially spherical diffuser.
Figure 4:
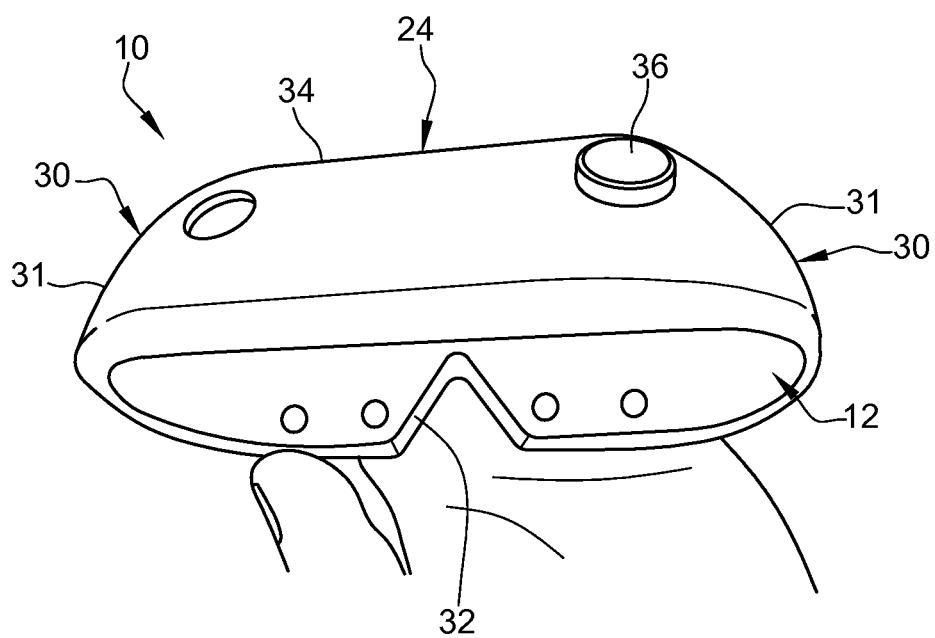

Most preferably, at least one among said at least two concave portions 22 is at least partially spherical to even more direct light emitted by the light source 14 toward user's eyes. The best homogeneity is obtained when the centre of curvature 28 of said at least one among said at least two concave portions 22 is the centre of the sphere. Preferably, centres of curvature 28 of both concave portions 22 are the centre of the sphere. FIGS. 3 and 4 show an embodiment of the binocular optoelectronic device 10 having a diffuser 12 with two partially spherical portions 30. Particularly, each spherical portion 30 forms a quarter sphere connected to each other by a central portion 24. Central portion 24 is preferably U-shaped to provide a continuous transition between the two spherical portions 30 to improve light homogeneity. Alternatively, the central portion 24 may be planar as shown on FIG. 2. In the case where the diffuser 12 comprises spherical portions 30, at least one light source 14 preferably comprises a light emitting axis oriented toward at least one among said centres of sphere. The combination of partially spherical diffuser 12 and a light source 14 oriented toward the centre of the sphere allows to improve the homogeneity of the light diffusion leading the light sensitivity measurement to be more accurate.

Regarding geometry parameter, i.e. position of the diffuser 12 with respect to the user's eyes, diffuser 12 is preferably configured to dispose the centre of curvature of each of concave portions 22 between an eye of the user and said concave portion 22. Particularly, diffuser 12 may be configured to dispose each of said centres of curvature in a transversal anatomic plane at the user's eyes. The more user's eyes are close to the centres of curvature, the more homogeneous the light will be received by the user. In the case where the diffuser 12 comprises at least partially spherical portions 30, the same geometry parameters may be applied to the diffuser 12 replacing said centres of curvature by said centres of the sphere.

Regarding material parameter, diffuser 12 may comprise an internal surface having an albedo of at least 80%, preferably of at least 90%, most preferably of at least 95%. In other words, the internal surface of the diffuser 12 is chosen to reflect the maximum intensity of light emitted by the light source 14. Furthermore, said internal surface is preferably a diffusely reflecting surface. In other words, there is equal luminance when viewed from all directions lying in the half-space adjacent to the surface. For example, the internal surface of the diffuser 12 may comprise a coating made of barium sulfate to have a diffusely reflecting surface with an albedo of at least 80%.

The diffuser 12 is preferably chosen to act as a light reflector of light but as diffusive as possible. It requires both a satisfactory reflection efficiency (great albedo) to be optically efficient and the ability not to have a specular reflection so that the output light seems very uniform despite the diffuser is enlighten by punctual light sources 14.

Some materials naturally have said both abilities, such as barium sulfate or Titanium Dioxide (TiO2). It is also possible to have pigments or white dyes in the material forming the diffusing surface to have a satisfactory albedo. A surface treatment may also be performed to suppress specular reflection, as managing surface roughness (graining), or with one or more coatings acting as anti-glare.

FIGS. 3 and 4 show a preferred embodiment of the binocular optoelectronic device 10 comprising a casing 31 forming a cavity 33 in which the diffuser 12 is lodged. As indicated above, diffuser 12 comprises in this embodiment two partially spherical portions 30 connected to each other by a central portion 24. The binocular optoelectronic device 10 may further comprise a cutout 32 configured to cooperate with the nose of the user to position the diffuser 12 in front of the user's eyes. To precisely position the diffuser 12 with regard to user's eyes, the binocular optoelectronic device 10 may also comprise a positioning surface 34 disposed at the opposite of the cutout 32 with respect to the diffuser 12 to contact user's forehead.

In the embodiment of FIGS. 3 and 4, the binocular optoelectronic device 10 comprises three light sources 14 disposed at the periphery of the diffuser 12 and directed to the centre of the sphere defined by the two partially spherical portions 30. Alternatively, a quasi-homogeneous light diffusion may be obtained with at least two light sources 14 each emitting light toward one of the concave portions 22 or partially spherical portions 30. Particularly, the diffuser 12 comprises holes in which light sources 14 are lodged. Preferably, light sources 14 are disposed near the positioning surface 34. Said positioning surface 34 may extend partially inside the cavity 33 to avoid light rays to be emitted from light sources 14 directly toward user's eyes.

The binocular optoelectronic device 10 may also comprise measuring means configured to determine at least one user parameter representative of the light sensitivity of the user. These measuring means preferably comprises a switch 36 reachable by the user on the periphery of the binocular optoelectronic device 10. This switch 36 allows the user to communicate to the binocular optoelectronic device 10 information representative of its light sensitivity. These measuring means mays also comprise sensors configured to be oriented toward the user's head. These sensors may detect or determine parameters representative of a user's response to light emission. The binocular optoelectronic device 10 may also comprise controlling means configured to provide at least one among: controlling the luminance of light emitted by said at least one light source 14, controlling the duration of the light emission, spatial repartition of the light emission and the spectrum of the light emission. Said controlling means may be inserted in the casing 31, for example behind the diffuser 12. Furthermore, binocular optoelectronic device 10 preferably comprises one or more battery configured to supply the at least one light source 14 and controlling means. Binocular optoelectronic device 10 may further comprise communication means configured to transmit information to an external module and/or to receive information from this external module. Said module may be a smartphone or a computer. Furthermore, the binocular optoelectronic device 10 may comprise a target configured to be disposed between user's eyes and the diffuser 12. Said diffuser 12 may also comprise at least one vision orifice (not shown) configured to be disposed in front of each user's eye by which the user can look through the binocular optoelectronic device 10. This at least one vision orifice allows to perform additional measurements regarding light sensitivity when the user look at external target. Preferably, the binocular optoelectronic device 10 comprises means for obstructing the vision orifice to perform light sensitivity threshold measurement.

In a preferred embodiment, the light source 14 is controlled with a constant current, i.e. the output of the light source 14 is constant. Despite this light control is rarely used because of its expensive design and heating issues, it allows to avoid any unwanted biological effects. Heating issues are preferably avoided by using one or more high power LEDs deliberately at a low power, as well as using passive heat sink. Indeed, Pulse Width Modulation (PWM) control is commonly used for controlling the LEDs but may generate unwanted biological effects.

In an additional embodiment, targets may be provided on the diffuser 12 to guide the gaze of the user.

The binocular optoelectronic device 10 is configured to be wearable by a user. In other words, dimensions and weight of the binocular optoelectronic device 10 are configured to make it possible for a user to handle it in front of its eyes using supporting means. Said supporting means may be its hands so that the user handles the binocular optoelectronic device 10 as binoculars. Alternatively, supporting means may be means for fastening the binocular optoelectronic device 10 to the user's head as straps able to surround the user's head. Alternatively, supporting means may be a support leg configured to sit on a table or on the ground. Support means are preferably removable from the binocular optoelectronic device 10.

To allow the binocular optoelectronic device 10 to be adapted to different morphologies, the diffuser 12 may have adjustable dimensions. Particularly, the diffuser's length may be variable to adjust the pupillary distance. To this end, the diffuser may be telescopic to adjust the distance between said two concave portions 22 or said partially spherical portions 30. In a preferred embodiment, binocular optoelectronic device 10 is dimensioned to receive therein an optical device worn by the user. Hence, light sensitivity may be measured while the user wears eyeglasses.

Figure 6:
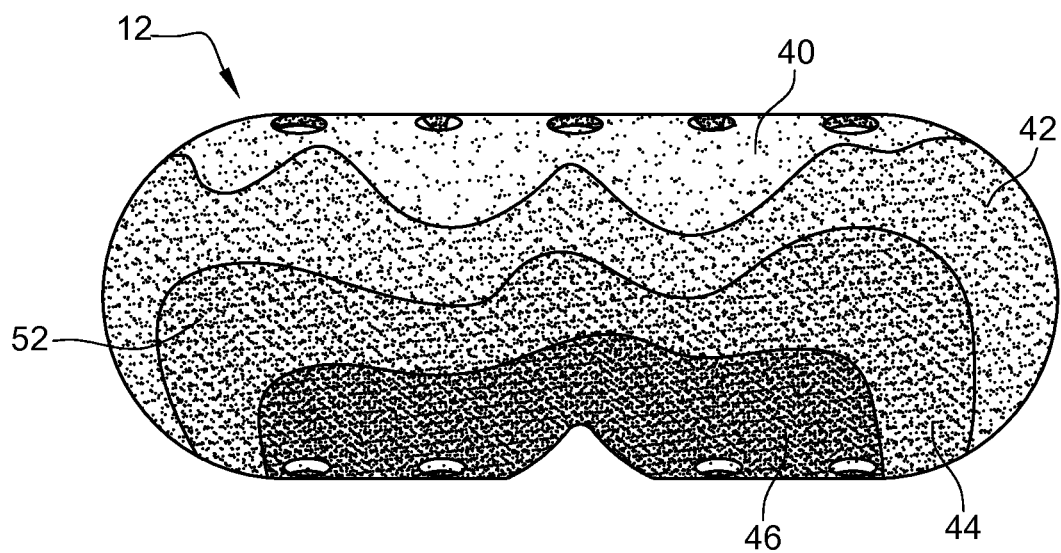
FIG. 6 schematically shows luminance distribution of the partially spherical diffuser of FIGS. 3 and 4.

FIG. 6 shows luminance distribution of the partially spherical diffuser 12 of the embodiment of FIGS. 3 and 4. The luminance distribution defines a first 40, a second 42, a third 44 and fourth 46 luminance areas corresponding to different luminance values. Luminance value of the luminance distribution increases from the first 40 to the fourth 46 luminance areas. Particularly, this luminance distribution extends from a minimum luminance value of 6500 cd/m$^2$ in the first luminance area 40 to a maximum luminance value of 7600 cd/m$^2$ in the fourth luminance area 46 with the three light sources 14 powered with a current of 330 mA. Applying the equation provided above to determine homogeneity of light diffusion provided by the diffuser 12, we can determine that homogeneity of light diffusion is here around 85.5%.

Figure 7:
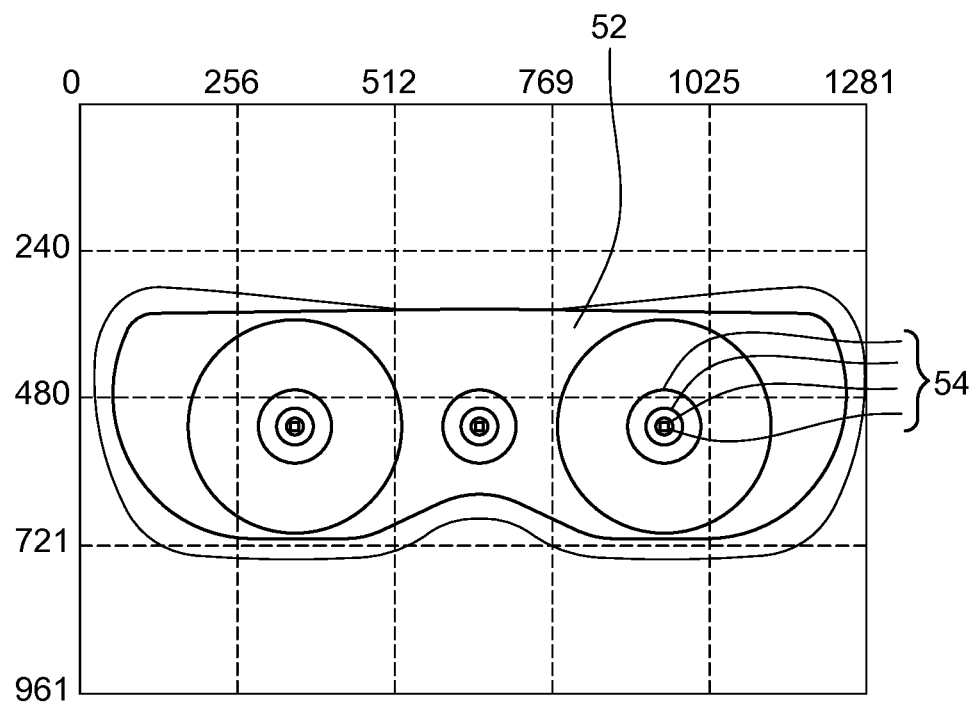
FIG. 7 schematically shows a plurality of planar measuring surfaces considered to determine the light homogeneity.

Tests have been performed using the measurement process described using the measuring device 50 and considering the circular areas 54 shown on FIG. 7. These measurements have been performed on the binocular optoelectronic device 10 having a partially spherical diffuser.

These measurements are gathered in five tables shown below and provides the homogeneity obtained when considering right and left circular areas 54 for different luminance values and light colors of the light emitted by the light source 14. We mean by "right and left circular areas" a predetermined area corresponding to the combination of one left and one right circular areas 54 of a same diameter representative of the light received by both left and right user's eyes. Therefore, the predetermined surface S which is considered for right and left circular areas 54 having a diameter of 52 mm is 4245 mm² (S=2×Π×52²/4).

TABLE 1

Homogeneity for left and right circular areas having a
diameter of 52 mm, i.e. a combined surface of 4245 mm²

|   | Light color | Luminance of the light source (Lux) | Homogeneity (%) |
|---|---|---|---|
| A | Cold | 500 | 58.28 |
| B | Cold | 1000 | 57.95 |
| C | Cold | 2000 | 57.66 |
| D | Cold | 4000 | 56.22 |
| E | Warm | 500 | 60.37 |
| F | Warm | 1000 | 60.27 |
| G | Warm | 2000 | 59.63 |
| H | Warm | 4000 | 58.44 |

It appears from table 1 that the diffuser 12 provides a light diffusion having a homogeneity of at least 55% when considering left and right circular areas 54 having a diameter of 52 mm, i.e. a predetermined surface of 4245 mm².

TABLE 2

Homogeneity for left and right circular areas having a
diameter of 26 mm, i.e. a combined surface of 1060 mm²

|   | Light color | Luminance of the light source (Lux) | Homogeneity (%) |
|---|---|---|---|
| A | Cold | 500 | 74.99 |
| B | Cold | 1000 | 75.26 |
| C | Cold | 2000 | 75.76 |
| D | Cold | 4000 | 75.13 |
| E | Warm | 500 | 77.83 |
| F | Warm | 1000 | 77.67 |
| G | Warm | 2000 | 77.91 |
| H | Warm | 4000 | 76.91 |

It appears from table 2 that the diffuser 12 provides a light diffusion having a homogeneity of at least 74% when considering left and right circular areas 54 having a diameter of 26 mm, i.e. a predetermined surface of 1060 mm².

TABLE 3

Homogeneity for left and right circular areas having a
diameter of 17.3 mm, i.e. a combined surface of 470 mm²

|   | Light color | Luminance of the light source (Lux) | Homogeneity (%) |
|---|---|---|---|
| A | Cold | 500 | 76.86 |
| B | Cold | 1000 | 75.26 |
| C | Cold | 2000 | 78.47 |
| D | Cold | 4000 | 78.64 |
| E | Warm | 500 | 82.43 |
| F | Warm | 1000 | 82.37 |
| G | Warm | 2000 | 82.22 |
| H | Warm | 4000 | 82.08 |

It appears from table 3 that the diffuser 12 provides a light diffusion having a homogeneity of at least 76% when considering left and right circular areas 54 having a diameter of 17.3 mm, i.e. a predetermined surface of 470 mm².

TABLE 4

Homogeneity for left and right circular areas having a
diameter of 8.7 mm, i.e. a combined surface of 115 mm²

|   | Light color | Luminance of the light source (Lux) | Homogeneity (%) |
|---|---|---|---|
| A | Cold | 500 | 84.18 |
| B | Cold | 1000 | 84.18 |
| C | Cold | 2000 | 84.66 |
| D | Cold | 4000 | 84.45 |
| E | Warm | 500 | 86.87 |
| F | Warm | 1000 | 86.53 |
| G | Warm | 2000 | 85.76 |
| H | Warm | 4000 | 85.77 |

It appears from table 3 that the diffuser 12 provides a light diffusion having a homogeneity of at least 84% when considering left and right circular areas 54 having a diameter of 8.7 mm, i.e. a predetermined surface of 115 mm².

TABLE 5

Homogeneity for left and right circular areas having a
diameter of 4.3 mm, i.e. a combined surface of 29 mm²

|   | Light color | Luminance of the light source (Lux) | Homogeneity (%) |
|---|---|---|---|
| A | Cold | 500 | 85.58 |
| B | Cold | 1000 | 85.41 |
| C | Cold | 2000 | 85.86 |
| D | Cold | 4000 | 86.37 |
| E | Warm | 500 | 92.42 |
| F | Warm | 1000 | 92.20 |
| G | Warm | 2000 | 92.07 |
| H | Warm | 4000 | 91.12 |

It appears from table 3 that the diffuser 12 provides a light diffusion having a homogeneity of at least 85% when considering left and right circular areas 54 having a diameter of 4.3 mm, i.e. a predetermined surface of 29 mm².

The shape and the size of said circular areas 54 have been defined to correspond to different stimulation of the user's eyes. Indeed, it is possible that light sensitivity process is managed both by cones and rods interactions. Hence, the stimulation of the user's eyes regarding light sensitivity depends on the shape and orientation of the light diffused toward the eyes. Thus, the shape, the position and the size of the circular areas 54 have been determined to represent different modes for stimulating cones and rods.

Said circular areas 54 have been determined to be representative of a sight cone having an angle from 36° to 3.1°, when considering a diameter of the circular area 54 from 52 mm to 4.3 mm, with the eyes of the user positioned at a distance of 80 mm from the bottom surface of the diffuser 12 and the center of the circular areas 54 being centered with regard to the user's line of sight. In this representation, the apex of the sight cone is positioned at the pupil of the user and the base of the sight cone is defined by the circular area 54 when the planar measuring surface is translated to be tangent to the bottom surface of the diffuser 12.

It has been determined that a single circular area 54 with a diameter lower than or equal to 4.3 mm specifically covers the retinal area of the user's eye. This retinal area mainly comprises the cones which are distributed on the both side of the fovea (+/−1.5°). In a similar way, it has been determined that a single circular area 54 with a diameter lower than or equal to 52 mm specifically covers an area of the retina stimulating both cones and rods in their maximum range of sensitivity. In fact, the density of cones and rods are optimal on the both sides of the fovea (+/−20° centered on the fovea).

Furthermore, the binocular optoelectronic device 10 may be provided with a filter configured to control light flux provided to the user's eyes or test its comfort in light condition. This filter may be a monocular or binocular occluder comprising different cutouts allowing to isolate selected areas of the diffuser 12. Alternatively, said filter may be an electrochromic glass configured to be disposed between user's eyes and the diffuser 12 to vary the user's perception of the diffuser 12. Alternatively or in combination, the filter may have a transmission value allowing to reduce the luminance of the homogeneous light flux provided to the user. Preferably, a plurality of filters with different transmission values may be provided to the binocular optoelectronic device 10 to determine the impact of these transmission values on the light sensitivity threshold. In a most preferable case, transmission values are chosen to correspond to transmission values that a photochromic lens may have depending on ultraviolet level. Furthermore, an ultraviolet source may be also provided to binocular optoelectronic device 10 to best simulate real light conditions. In this latter case, the binocular optoelectronic device 10 is preferably provided with a filter able to filter ultraviolet so as to protect the user from this ultraviolet source.

The present invention also provides a method for measuring a light sensitivity threshold of a user with a binocular optoelectronic device 10 as described above. The user is first equipped with the binocular optoelectronic device 10 with the diffuser 12 facing user's eyes. In the embodiment of FIGS. 3 and 4, each eye of the user is aligned with a center of the sphere. Then, the user is provided with a quasi-homogeneous light diffusion from light emitted by said at least one light source 14. A light sensitivity threshold of the user is finally determined depending of at least one user parameter. Step of providing the user with a quasi-homogeneous light diffusion may comprises a step of varying the luminance of light emitted by said at least one light source 14. Hence, an increase or decrease of light intensity may be provided to the user. Preferably, the varying step comprises increasing light luminance so as to start light emission with a comfortable luminance for the user. Furthermore, light sensitivity threshold is easier to determine when the luminance is increased than the opposite. The light sensitivity threshold is determined when a predetermined user parameter value or state is detected. For example, when the binocular optoelectronic device 10 comprises a switch 36, the user may choose himself when the luminance is uncomfortable by pressing the switch 36. User's light sensitivity threshold may be determined depending to the luminance at which the user pressed the switch 36.

To improve the accuracy of the light sensitivity measurement, said method may comprise a predetermined scenario wherein the varying step comprises two successive detecting steps corresponding to different discomfort states of the user. Varying step may comprise a first step of detecting a first user parameter representative of a first light sensitivity value of the user at a first luminance value and a second step of detecting a second user parameter representative of a second light sensitivity value of the user at a second luminance value. Then, user's light sensitivity threshold is determined depending on at least one among the first and second user parameters. When the binocular optoelectronic device 10 comprises a switch 36, the first user parameter may be a first switch press representative of a starting light discomfort and the second user parameter may be a second switch press representative of a high light discomfort. It has been observed that when the user is asked to step his light discomfort by at least two switch presses, he is able to better evaluate his maximum light discomfort.

Said varying step may be performed by the user himself. The user may vary the luminance of the light source 14 and the kinetics of this variation. In this case, determining step may comprise a step of determining the luminance variation and the kinetics thereof.

Furthermore, said varying step may further comprise varying the spatial repartition of the light emission and/or the spectrum of the light emission, alternatively or in combination to the luminance variation of the light emitted by the light source 14.

Moreover, the binocular optoelectronic device 10 preferably comprises a cover which allows to prevent parasitic light beams, i.e. other light than those provided by the light source 14, to enter within the binocular optoelectronic device 10 when placed against the user's face. Most preferably, the cover is made from a flexible material allowing to provide a contacting surface with shape complementary to the user's face. This flexible material is for example a soft and flexible polymer.

The invention claimed is:

1. A binocular optoelectronic device wearable by a user to measure a light sensitivity threshold of the user, the device comprising:
a concave device configured to face eyes of the user, the concave device defining a cavity, the concave device comprising at least two concave portions having a center of curvature distinct from each other, each of the concave portions being configured to be disposed on each side of a planar central portion and in front of one of the eyes of the user when the binocular optoelectronic device is worn; and
at least one light source configured to emit light toward said concave device,
wherein the concave device comprises predetermined parameters comprising at least one of shape, geometry, and material of the concave device, the predetermined parameters providing a quasi-homogeneous light diffusion with a homogeneity of at least 55% to both of the eyes of the user from the light emitted by said at least one light source.

2. The binocular optoelectronic device according to claim 1, wherein the homogeneity is determined based on the luminance distribution diffused by the concave device and projected on a planar measuring surface, and
wherein the homogeneity is determined with respect to at least one predetermined area of said planar measuring surface.

3. The binocular optoelectronic device according to claim 2, wherein said at least predetermined area is circular.

4. The binocular optoelectronic device according to claim 3, wherein the homogeneity is at least 55% with a predetermined area equal or lower than 4245 mm$^2$.

5. The binocular optoelectronic device according to claim 1, wherein at least one of said at least two concave portions is at least partially spherical, the center of curvature of said at one of said at least two concave portions being the center of the sphere.

6. The binocular optoelectronic device according to claim 1, wherein the concave device is configured to dispose the center of curvature of one of the concave portions between one of the eyes of the user and said concave portion.

7. The binocular optoelectronic device according to claim 1, wherein the binocular optoelectronic device is dimensioned to receive therein an optical device worn by the user.

8. The binocular optoelectronic device according to claim 1, wherein said at least one light source is disposed at the periphery of the concave device.

9. The binocular optoelectronic device according to claim 1, wherein said at least one light source comprises a light emitting axis oriented toward at least one of said centers of curvature.

10. The binocular optoelectronic device according to claim 1, wherein the concave device comprises an internal surface having an albedo of at least 80%.

11. The binocular optoelectronic device according to claim 1, further comprising:
- a sensor configured to determine at least one user parameter representative of the light sensitivity of the user; and
- a controller configured to one of: control the luminance of light emitted by said at least one light source, control the duration of the light emission, control spatial repartition of the light emission, and control the spectrum of the light emission.

12. A method for measuring a light sensitivity threshold of a user, the method comprising:
- providing the user with the binocular optoelectronic device according to claim 1;
- providing the user with the quasi-homogeneous light diffusion from the light emitted by said at least one light source; and
- determining a light sensitivity threshold of the user depending on at least one user parameter.

13. The method according to claim 12, wherein the providing the user with the quasi-homogeneous light diffusion comprises varying the luminance of light emitted by said at least one light source.

14. The method according to claim 13, further comprising, during the varying:
- detecting a first user parameter of the at least one user parameter, the first user parameter being representative of a first light sensitivity value of the user at a first luminance value, and
- detecting a second user parameter of the at least one user parameter, the second user parameter being representative of a second light sensitivity value of the user at a second luminance value,
- wherein said light sensitivity threshold is determined depending on at least one of the first and second user parameters.

15. The binocular optoelectronic device according to claim 1, wherein the homogeneity is at least 60%.

16. The binocular optoelectronic device according to claim 1, wherein the homogeneity is at least 70%.

17. The binocular optoelectronic device according to claim 4, wherein the homogeneity is at least 74% with a predetermined area equal or lower than 1060 mm$^2$.

18. The binocular optoelectronic device according to claim 4, wherein the homogeneity is at least 76% with a predetermined area equal or lower than 470 mm$^2$.

19. The binocular optoelectronic device according to claim 4, wherein the homogeneity is at least 84% with a predetermined area equal or lower than 115 mm$^2$.

20. The binocular optoelectronic device according to claim 4, wherein the homogeneity is at least 85% with a predetermined area equal or lower than 29 mm$^2$.

* * * * *